(12) United States Patent
Pina et al.

(10) Patent No.: US 6,507,400 B1
(45) Date of Patent: Jan. 14, 2003

(54) OPTICAL SYSTEM FOR MULTI-PART DIFFERENTIAL PARTICLE DISCRIMINATION AND AN APPARATUS USING THE SAME

(75) Inventors: Jean-Charles Pina, Duncanville, TX (US); Wieland von Behrens, Hillsborough, CA (US); Mervin L. Gangstead, Garland, TX (US); James R. Boyd, Plano, TX (US); Jerry B. West, DeSoto, TX (US)

(73) Assignee: MWI, Inc., Dallas TX ( * ) Notice: Subject to any disclaimer, the term of this patent is extended or adjusted under 35 U.S.C. 154(b) by 0 days.

(21) Appl. No.: 09/507,429

(22) Filed: Feb. 19, 2000

Related U.S. Application Data (60) Provisional application No. 60/121,131, filed on Feb. 27, 1999.

(51) Int. Cl.[7] ................................................ G01N 21/00
(52) U.S. Cl. ..................................................... 356/338
(58) Field of Search ................................ 356/337–343, 356/349, 38, 73, 442, 318, 72, 317; 250/573–575, 461.2

(56) References Cited

U.S. PATENT DOCUMENTS

| | | | |
|---|---|---|---|
| 2,656,508 A | 10/1953 | Coulter | 324/71 |
| 3,502,973 A | 3/1970 | Coulter et al. | 324/71 |
| 3,502,974 A | 3/1970 | Coulter et al. | 324/71 |
| 3,661,460 A | 5/1972 | Elking et al. | 356/36 |
| 3,710,993 A | 1/1973 | Collin | 223/91 |
| 3,871,770 A | 3/1975 | von Behrens et al. | 356/103 |
| 3,989,381 A | 11/1976 | Fulwyler | 356/39 |
| 4,070,113 A | 1/1978 | Frazer et al. | 356/104 |
| 4,110,043 A | 8/1978 | Eisert | 356/102 |
| 4,284,412 A | 8/1981 | Hansen et al. | 23/230 B |
| 4,348,107 A | 9/1982 | Leif | 356/72 |
| 4,420,720 A | 12/1983 | Newton et al. | 324/71.4 |
| 4,515,274 A | 5/1985 | Hollinger et al. | 209/3.1 |
| 4,527,114 A | 7/1985 | Coulter | 324/71.1 |
| 4,541,719 A | 9/1985 | Wyatt | 356/343 |
| 4,616,927 A | 10/1986 | Phillips et al. | 356/338 |
| 4,693,602 A | 9/1987 | Wyatt et al. | 356/356 |
| 4,710,021 A | 12/1987 | von Behrens | 356/72 |
| 4,915,501 A | 4/1990 | Steen | 356/343 |
| 4,953,978 A | 9/1990 | Bott et al. | 356/336 |
| 5,017,497 A | 5/1991 | Gerard dee Grooth et al. | 436/63 |
| 5,056,918 A | 10/1991 | Bott et al. | 356/336 |
| 5,104,221 A | 4/1992 | Bott et al. | 356/336 |
| 5,125,737 A | 6/1992 | Rodriguez et al. | 365/39 |
| 5,129,723 A | 7/1992 | Howie et al. | 356/336 |
| 5,138,181 A | 8/1992 | Lefevre et al. | 250/573 |
| 5,378,633 A | 1/1995 | von Behrens et al. | 436/63 |
| 5,895,869 A | 4/1999 | von Behrens et al. | 73/865.5 |
| 5,983,735 A | 11/1999 | von Behrens et al. | 73/865.5 |
| 6,067,157 A | * 5/2000 | Altendorf | 356/337 |

FOREIGN PATENT DOCUMENTS

EP  0 311 655 B1  11/1994

OTHER PUBLICATIONS

Gary C. Salzman, "Light Scattering Analysis of Single Cells", Cell Analysis vol. 1, pp. 111–143, 1982.

(List continued on next page.)

*Primary Examiner*—Michael P. Stafira
(74) *Attorney, Agent, or Firm*—Sidley Austin Brown & Wood LLP (57) ABSTRACT

The present invention relates to an optical system for an apparatus for multi-part differential particle discrimination to facilitate analysis, classification, and sorting of various fluid components for presentation. The optical system is characterized by one or more of the following: a synchronized illumination beam and flow cell conduit, a flow cell arrangement to control back reflection, and light sensor arrangement to particularly gather a specific range of light scatter, such specific range of light scatter directly corresponding to at least one type of particle capable of being identified by the apparatus.

36 Claims, 4 Drawing Sheets

OTHER PUBLICATIONS

Leon L. Wheeless, Jr. and David B. Kay, "Optics, Light Sources, Filters, and Optical Systems", Flow Cytometry: Instrumentation and Data Analysis, pp. 21–76, 1985.

Warren Groner and Elkin Simson, "Practical Guide to Modern Hematology Analyzers", pp. 1–241, 1995.

Kaoru Takarada, "Flow Cytometers—History and Measurement Principle–", Flow Cytometry: Instrumentation and Data Analysis, Sysmex Journal International vol. 6, No. 1, pp. 83–90, 1996.

Francis A. Jenkins and Harvey E. White, "Fundamentals of Optics", Third Edition, pp. 1–27, 1957.

A. Schwartz and Emma Fernández–Repollet, "Standardization for Flow Cytometry", Methods in Cell Biology, vol. 42, Flow Cytometry, Second Edition, Part B, Chapter 35, pp. 605–626, 1994.

\* cited by examiner

OPTICAL SYSTEM FOR MULTI-PART DIFFERENTIAL PARTICLE DISCRIMINATION AND AN APPARATUS USING THE SAME

This application claims the benefit of Provisional application No. 60/121,131, filed Feb. 27, 1999.

FIELD OF THE INVENTION

The present invention relates to devices and methods for the discrimination of particulate elements using flow analysis in walled conduits, and more particularly, to devices and to methods for optically discriminating particulate elements on the basis of different light scattering effects and different light emission behaviors stemming from structures (or substructures) of such elements as well as from differences in general compositional element characteristics.

BACKGROUND OF THE INVENTION

Since establishment of the Cell Theory in the 1840's clinicians have found it informative to categorize, analyze and monitor the diverse blood cell populations of man and beast. In the blood of any typical mammal these cells are the erythrocytes, leukocytes and thrombocytes. Their numerical concentration can be estimated with precision; provided however, sufficient cells are counted.

In health, mammals have five subpopulations of circulating leukocytes: neutrophil granulocytes, lymphocytes, monocytes, eosinophil granulocytes and basophil granulocytes. Since perfection of the light microscope around 1880 and the introduction of Ehrlich's dyes for differentiating the granulocyte's granules shortly thereafter, these leukocyte subsets can also be differentiated with precision; provided however, sufficient cells are examined. Additionally there is a need for rapid exact analysis of countless other suspendable complex micro-particles and cell types.

During last century it became clear from optic scattering effects and from other evidence that, even though proteins could not be resolved with classic microscopes and were in nanometer size ranges, these too must be considered micro-particles.

Whilst counting chambers and microscopes could be used for cell evaluations, investigators performing these tasks were prone to fatigue and subjective vagaries. Therefore, in relation to known statistical sampling errors, an inadequate number of micro-particles could be analyzed by microscopy and only extreme pathological deviations were intercepted reliably. On the other hand, by 1930 R. A. Fisher had taught that, if a sufficient number of well-chosen, different, robust measurements were made on complex organic entities such as cells during an investigation, then, it would be straightforward to objectively assign the different tested elements to appropriate natural sets and subsets.

From the 1930's onwards attempts were made to automate the time-consuming number-accumulation chore and classification challenge of cell and micro-particle analysis. For clinical cell analysis, these endeavors evolved along two main paths: (i) image analysis microscopy, which examines all microscopic objects, and (ii) flow analysis, or generalized flow cytometry of micron-sized and of sub-micron particles down to macromolecules.

In classical microscopy a large specimen is placed into an object plane which is orthogonal to the optic axis of the microscope. That classical plane is occupied by a vast expanse of sample material which is illuminated over a wide field, i.e., a field much larger in area (and frequently also in depth) than the arbitrarily definable voxel (or volume element or "cell of space") occupied, for example, by a small single tissue cell or by an ensemble of granules within, perhaps, an eosinophil cell or a suspension or solution in a spectrophotometric cuvette. In whatever manner the voxel (or "cell") is defined, there is a very vast number of these illuminated elements in the classical microscopic object. Each such illuminated voxel of such a sample preparation causes the scattering (or, in certain settings fluorescence) of light. In relation to the signal light from a specific voxel of interest, the light from all the other structures in the microscopic field represents signal-degrading background noise. That background noise light can easily exceed 99.9% of the total light received in the microscope's image location of the specific voxel. Hence, significant detail relating to such classically viewed voxels is likely lost to the viewer.

"Confocal" microscopy is an automated technique for avoiding the degrading effects of that frequently overwhelming background noise discussed above. The background is avoided by contemporaneously having both the illumination lens system(s) and the interrogation lens system(s) focus essentially on one voxel at a time. Additionally, computer techniques are used to synthesize three-dimensional high-signal images whose rich information content could not otherwise be captured. Confocal microscopy was first patented in the United States in 1952 by Marvin Minsky. Today, such technique is practiced via instruments which matured in the 1980's (see, for example, S. W. Paddock "Confocal Laser Scanning Microscopy" BioTechniques 27 992–1004 1999).

Thus, in the centuries-old field of microscopy the relatively recent introduction of the optic background-noise-reducing confocal microscopy technique has advanced the classic approach beyond illumination of the entire surrounding tissue to specific illumination and interrogation of optically-isolated elements of space, which can be made smaller than individual biologic cells. This lowers the limit of detection by increasing the signal-to-background ratio that can be differentiated as a separate element in the colloquial signal/noise function for any analyte or measurand. Without the confocal microscopy approach the sample signal is lost in the "sea" of system noise.

Returning now to the evolution of particle flow analysis, by the mid-century it has been said that considerable work had been done to produce instruments capable of counting blood cells. Interestingly, such instruments varied considerably in principle, mode of operation, complexity and cost.

Prior to the work of Crosland-Taylor in this area, optic flow cytometry evolved via the upright optic axis of the microscope with an object plane that was orthogonal to the optic axis. Crosland-Taylor made significant progress in overcoming the optic tissue background noise interference problem of microscopy by exploiting hydrodynamic forces within an optically clear suspension fluid to present biologic cells singly to an optic interrogation area in a so-called hydrodynamically focused cell monofile.

Throughout micro-particle analysis, one broad approach had been to suspend particulates in an appropriate fluid (e.g., as aerosol or hydrosol) in order to isolate a "sample" away from other interfering objects so that ensembles (down to single elements) could be interrogated in physically isolated elements of space. Specific sensors could then respond quantitatively to differing properties of the isolated elements. In this way multi-angle light scatter (MALS) studies had already allowed the interrogation of particle ensembles in the middle of cylindrical cuvettes (i.e., interrogation cells) far from the surrounding walls. The Crosland-Taylor work implemented a general approach to isolating thin, stable filaments of particulate-containing fluid for interrogation in flow-through cells rather than merely in static cells or cuvettes.

When lasers were introduced, MALS could more appropriately be termed MALLS (multi-angle laser light scatter); and in the 1960's many scientists incorporated lasers into the earlier Crosland-Taylor flow cytometry systems. Thereby, additional optic sensing axes could be placed into the traditional orthogonal microscopic object plane which had been co-opted by flow cytometry for the particle monofile; and the illuminating laser pencil for flow cytometry could also reside in that plane. Indeed, many in the art perceived that an interrogation apparatus could be arranged with laser and particle filament intersecting at the optic scattering and fluorescence origin of a spherical radiation domain. Crosland-Taylor had already introduced bubble-free degassed carrying liquids. Therefore, except for the thin sample fluid filament carrying the test particulates through a finite illuminated radiation centroid, this spherical scattering space was occupied only by optically clear fluid in which the illuminating laser pencil need not leave a trace.

Such system enabled rapid MALLS examination of stained or unstained particles ranging in size from protein molecules through bacteria and mammalian cell organelles to large organic cells. Additionally, non-optic sensors such as electrical impedance and capacitance cell interrogation principles could be applied to each larger particle, whether concurrently with an optical interrogation or in exact tandem synchronization—of a type which had evolved in the flow cytometry subfield of cell sorting (e.g., U.S. Pat. Nos. 3,710,933 and 3,989,381).

By the 1970's flow cytometry could measure a host of both "intrinsic" and "extrinsic" particle properties. The so-called "intrinsic properties" can be documented without the use of special reagents while "extrinsic" properties are elicited via physical, chemical or biological reagents such as altered pH or tonicity and/or dyes and/or coupled monoclonal antibodies or tags.

Figure 1A:
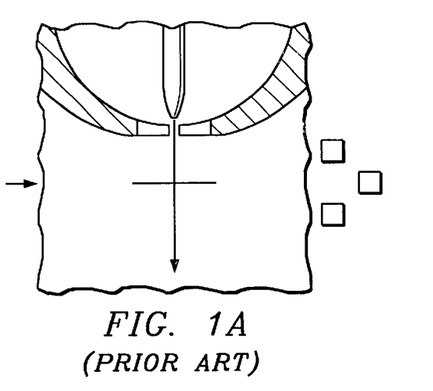
FIG. 1A illustrates a conventional arrangement for optical interrogation of a precise particle monofile in a vast wall-illumination-avoiding fluid space.
Figure 1B:
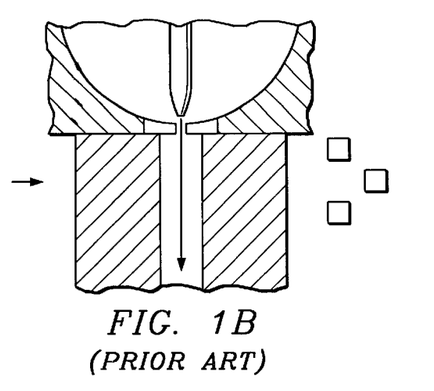
FIG. 1B illustrates a conventional arrangement for optical interrogation of a precise particle monofile in a conduit-bounded fluid space.

FIGS. 1A and 1B summarize the state of flow analysis transducers in the 1970's. These figures were based on work performed to produce vortex-assisted, super-focused, low-variance, low-noise, many-centimeter-long cell monofiles. In particular reference to the "tank" of FIG. 1A, U.S. Pat. No. 5,138,181 teaches that even without induction of a vortex "the fact that the positioning of the flow is provided by positioning the counting orifice, makes the alignment of the optical beam on the flow extremely stable."

Hydrodynamic focusing of the sample stream at the top results in a particulate filament, or monofile, which is stabilized by additional primary upstream and secondary downstream sheath inflows in both FIGS. 1A and 1B. This monofile jets through the impedance, laser, and other interrogation regions that are indicated schematically in the "tank" of FIG. 1A and about the "conduit" of FIG. 1B. That a secondary downstream sheath satisfied the Venturi needs of the jet not only in the "tank", but, via fully stable countercurrent flow, also in the "conduit" was verified by the teachings of U.S. Pat. Nos. 4,515,274, 4,710,021, 5,378,633, 5,895,869, and 5,983,735.

Figure 1C:
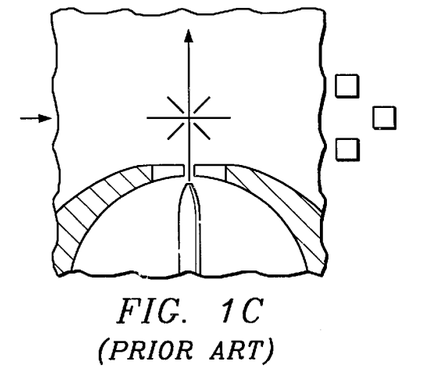
FIG. 1C illustrates a conventional vast wall-illumination-avoiding fluid space capable of sub-micron particle size interrogation.
Figure 1D:
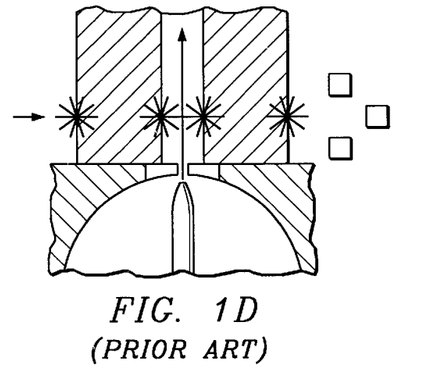
FIG. 1D illustrates a conventional conduit-bounded fluid space and highlights those structural limitations that inhibit successful sub-micron particle size interrogation.

From U.S. Pat. Nos. 4,710,021, 5,378.633, 5,895,869, and 5,983,735, it is taught that in many types of focused flow analysis the flow axes could be in any spatial direction. As shown in FIGS. 1C and 1D hereof, for bubble control the flow directions are generally arranged vertically upward when a compound transducer is not incorporated into systems that perform physical cell sorting. Using the stabilizing vortex lever Eisert also maintained very precisely located very thin monofiles in horizontal micrposcope object planes in what are essentially the "flat chambers" of familiar hemocytometers (see U.S. Pat. No. 4,110,043).

The dual structures of FIGS. 1A–1D symbolize a two decade schism in the sub-domain of flow analysis that exploited optic scatter:

1. scatter system flow analysis of sub-micron scatter structures in wall-illumination-avoiding fluid spaces, for example, the tank transducers of FIGS. 1A and 1C; and
2. scatter system flow analysis of supra-micron scatter structures in wall-illumination-degraded conduit bounded fluid spaces, for example, the conduit transducers of FIGS. 1B & 1D.

This dichotomy in scatter sensitivity did not extend to the thriving fluorescent applications of flow cytometry. Fluorescence system flow analysis of supra-micron scatter, fluorescent structures, and of sub-micron fluorescent (but not scatter) structures use conduit bounded fluid spaces such as that illustrated in FIGS. 1B and 1D. Of the sensors illustrated, they can take the form of either a coarse scatter sensor or a fluorescent sensor. If including a fluorescence sensor, then all incident-wavelength scatter noise (and scatter signal) is routinely filtered out from the longer emitted-wavelength measurements of these systems. With respect to fluorescent particle interrogations, these systems effectively reduce to that illustrated in FIG. 1C and do confocal fluorescent flow cytometry.

In the early 1970's one of the desires of flow cytometry became recognition of "intrinsic" optic scatter of sub-microscopic structures such as bacteria, organelles and characteristics of small cells such as platelets. During this time, MALS explorations using helium-neon laser and argon ion laser Biophysics Cytograph systems with both circular and square cross-sections were conducted. However, when looking for the sub-microscopic scatter substructures known from electron microscopy (as opposed to also known fluorescent sub-micron substructures) it became evident that, despite the great improvements in hydrodynamic focusing made available per U.S. Pat. No. 3,871,770, there was a fundamental problem of signal-degrading optic scatter background noise in affordable walled transducer derivatives (e.g., FIG. 1B).

FIG. 1C shows diagrammatically that, in the wall-illumination-avoiding setting, micro-particles such as bacteria or cellular granules or macromolecules, do generate highly informative MALLS signatures which can be sampled over almost $4\pi$ steradians about any angle outside the intense 13° narrow-angle forward scatter cone.

Of course, the micro-particle illustrated in FIG. 1D also generates the same unique MALLS signals in the wall-illumination-degraded conduit structures. Unfortunately, using any of the available conventional flow cytometry illumination arrangements, the walls of these walled-conduit structures conventionally generates such an enormous quantity of background scatter noise, that, for practical purposes, the unique MALLS signatures from sub-micron structures can not be usefully discriminated therefrom. The improved positional, orientational and temporal variance that was enabled by spiral hydrodynamic focusing to overcome excitation field inhomogeneities was totally wasted in the optic scatter setting of walled-conduit flow cuvettes.

By the 1980's Crosland-Taylor's optic transducer flow cells had undergone numerous modifications and design variations (see, for example, U.S. Pat. No. 3,661,460). However, in each typical flow cell there had to be a physical boundary between the fluid medium carrying the particles and the media through which the illuminating light entered and left the fluid in the flow cell. Since these interfaces could never be optically perfect, they always gave rise to some light scatter noise. Rectangular conduits assembled from polished planar slabs could have optically quiet faces; however, the corner edges of those conduits always scattered the typically-used broad flat ribbons of illuminating laser light very intensely. With these ellipsoidal illumination ribbons, round walled conduits gave rise to enormous additional diffraction scatter degradations. Hence, after around 1980 practical attempts at collecting MALLS signals from regions intermediate between the orthogonal forward and lateral faces of classical rectangular flow cytometry flow cells of the type shown in FIGS. 1B and 1D were essentially abandoned.

Of all the focused illuminating light in such classical flow cytometry, far less than 1% will be intercepted by even a large particulate element of interest. Of such tiny intercepted fraction of light, far less than 1% will be scattered by the particle as signal light. If the particle is larger in diameter than the wavelength of the illuminating light, say a granulocyte examined with a helium-neon laser light, then far less than 1% of that scattered signal light is scattered in directions other than the narrow-angle forward direction (of an acceptance cone half-angle of, e.g., 13% from the optical axis of the laser).

As stated above, it has been known since around 1900 that particles of the order of size of the wavelength of the illuminating light, say the 300 nm to 700 nm eosinophilic granules within eosinophilic granulocytes, will scatter a relatively high proportion of characteristic signal light in the spatial region between said forward cone and the orthogonal or lateral direction. However, sub-micron particles additionally have a greatly reduced scattering efficiency with a scattering cross-section as low as 1% of geometrical cross-section around 100 nm (see U.S. Pat. No. 4,693,602). To this end, what became clear in the 1970's in flow cytometry studies associated with U.S. Pat. No. 3,871,770 using walled-conduit flow cells was that, even if monochromatic laser light (rather than polychromatic mixed light) is used at around the wavelength of white light, then the signal for typical organic cells and microorganisms is almost totally degraded by scattered light from any close wall edges as in FIG 1D. Therefore sub-microscopic particles could not be analyzed sensitively in these classical flow cytometry flow cells by the MALLS techniques, which had been shown by some, theoretically and practically, to give the right discriminations; provided however, wall-illumination-avoiding analytical conditions are used.

Recapitulating, FIG. 1A shows a conventional wall-illumination-avoiding optic "tank". In such an arrangement, hydrodynamically focused particulates generally pass from an impedance and/or capacitance or RF sensor into a fluid body which is so vast in relation to a particle file interrogated by a laser beam that optic irregularities at the very distant walls through which the laser enters and exits the fluid can be arranged to contribute mathematically negligible background noise to appropriate scatter signals gathered as in confocal microscopy at the illuminated center of a vast conceptual spherical radiation domain. FIG. 1B shows a wall-illumination-degraded optic "conduit". In such a construction, hydrodynamically focused particulates generally pass from an impedance and/or capacitance or RF sensor into a transparent walled conduit flow cell. In such a typical clinical flow cytometry arrangement, the interrogated particle file is so close to the optically irregular flow cell walls that optic background noise scattered from those walls or edges overwhelms scatter signals from sub-micron particles. This happens not only when the conduit cross section is circular but also when that cross section is square or rectangular, for example, the cost-effective 250 $\mu$m×250$\mu$m (flow path dimensions), polished flow cells (Part No. 131.050-QS, Hellma, Corp.) which have been routinely available since the 1980's.

This signal/noise scatter problem in walled-conduit flow cells was summarized in U.S. Pat. No. 4,515,274. The reference provides that, "the smaller the size of the flow cell 16, the better its optical characteristics, in that the flow cell approaches a point source for optical signals." As can be seen from this rationale, it is not conventionally the biological cell or micro-particle that is considered as the point source for the harvested optical signals, but the more than 10,000-fold larger illuminated flow cell. Unquestionably, the scatter signal from a biologic cell only rises with difficulty above the optic noise produced from such conventional systems. For more modern systems, this issue remains unresolved.

As opposed to addressing the generation of such background noise, enormous masking efforts and diffraction blocking is practiced in/by conventional systems to get the signal at the advocated and implemented single intermediate "MALS" scatter sensor to rise above the prevalent scatter noise. By contrast, in "tanks" without a wall-proximity and without that circular orifice diffraction scatter, the interception of innumerable low-noise MALLS signals has been systematically routine since the 1970's.

To this end, an exemplary modern system is illustrated in U.S. Pat. 5,125,737. Such system, which is similar to that illustrated in FIG. 1D, does not teach any means for avoiding the generation of the overwhelming background noise scatter of FIG. 1D. Indeed, that patent essentially accepts as a conclusion that such background noise will be generated and that it is desirable to simply block out as much of the undesirable noise scatter as possible.

Since the 1940's, it has been recognized that making optic measurements essentially simultaneously at differing scattering angles greatly assists in coping with the effect of inevitable degrading background noise. This is because, as in exploitation of the "common mode rejection ratio" technique which has long been used in electronic relationships, if a systematic error occurs in one measurement, and a basically similar systematic error is introduced in the coupled measurement, then the data can frequently be viewed in such a way that even large errors tend to cancel each other out. Thus, the measurements are no longer stochastically independent.

Formally, a "common mode rejection ratio" is measured in decibels and might here be defined as 20 log (I/$\Delta$i), wherein I is the absolute signal intensity at one selectably relevant robust broad annular scatter angle cone (e.g., at 13°), and $\Delta$i represents a difference between intensity values in certain measuring and reference scatter cones (e.g., a 13° cone and a "missing" MALLS cone). This second cone should not be the ubiquitous 90° cone, as the scatter intensity has fallen off too greatly for supra-micron particle applications so far out. The second cone should be greater than 13° but less than 90°; but classically, any arbitrarily selected single-angle cone in this region has been difficult to maintain from system to system when a full MALLS sensor series was not manufactured directly into one of the complex flow cells.

Accordingly, a need exists for a system having a walled-conduit that receives a particulate-carrying fluid filament and is subjected to an emitted laser beam for purposes of particulate discrimination to minimize light scatter background noise produced by an interaction of the walled-conduit and the laser beam. Moreover, a further need exists for such a system to provide sufficient reference and measurement scatter, produced from the laser beam-conduit interaction, to facilitate reliable application of the common mode rejection ratio technique.

SUMMARY OF THE INVENTION

At least one aspect of the present invention is drawn to a particle analyzing apparatus for discriminating particulate element(s) in a fluid flow for purposes of analysis, classification, sorting, and presentation. The apparatus has an illumination source for emitting an illumination beam, a flow cell, and a light sensor. The flow cell has: a flow passage, through which a fluid flow containing particles can pass, a first exterior face perpendicular to a first axis of the flow cell, and a second exterior face perpendicular to a second axis of the flow cell. Of note, the first axis is substantially co-axial with an illumination beam emitted from the illumination source, and the first exterior face and the second exterior face are orthogonal. The light sensor, oriented substantially parallel to the second exterior face of the flow cell and displaced a sufficient distance from the second axis to enable receipt of a prescribed range of light passed by the first exterior face, operatively receives light from the illumination source via the flow cell.

Another aspect of the present invention is directed to a particle analyzing apparatus for discriminating particulate element(s) in a fluid flow for purposes of analysis, classification, sorting, and presentation. The apparatus includes an illumination source to emit an illumination beam, a flow cell, a sample supply, and a first light sensor. The flow cell has: a flow passage extending through the flow cell, a rear surface portion that receives an illumination beam emitted by the illumination source, and a forward surface portion that passes light formed from an illumination beam received by the rear surface portion. The flow cell has a first axis, which is substantially co-axial with an axis of an illumination beam emitted from the illumination source, and a second axis, which is orthogonal to the first axis. The sample supply operates to introduce a fluid to the flow passage of the flow cell. The first light sensor operates to receive at least light passed from the flow cell in response to an interaction with an illumination beam emitted by the illumination source and a fluid supplied to the flow passage of the flow cell. A light receiving surface of the light sensor is substantially parallel to the axis of an illumination beam emitted from the illumination source, and the first light sensor is displaced a prescribed distance from the second axis.

Another aspect of the present invention is directed to a particle analyzing apparatus for discriminating particulate element(s) in a fluid flow for purposes of analysis, classification, sorting, and presentation. The apparatus has an illumination source to emit an illumination beam along an optical axis of the apparatus. Moreover, the apparatus includes a flow cell, a sample supply, and a light sensor. The flow cell, positioned along the optical axis, has a flow path extending through the flow cell as well as a portion of an exterior surface to receive an illumination beam emitted from the illumination source. The flow cell is oriented to prevent formation of back reflection, parallel to the optical axis, in response to an emission of an illumination beam from the illumination source. The sample supply functions to introduce a fluid to the flow path of the flow cell. The light sensor, positioned along the optical axis, operates to receive at least light passed from the flow cell in response to an interaction with an illumination beam emitted by the illumination source and a fluid supplied to the flow passage of the flow cell.

Another aspect of the present invention is directed to an optical system for a particle analyzing apparatus for discriminating particulate element(s) in a fluid flow for purposes of analysis, classification, sorting, and presentation. The apparatus includes an illumination source for emitting an illumination beam and at least one light sensor to receive at least a light component of an emitted illumination beam. The optical system includes a focusing optical system and a flow cell. The focusing optical system, positioned along an optical axis of the system, operates to receive an illumination beam emitted by the illumination source. The flow cell, positioned along an optical axis of the system and prior to the at least one light sensor, has: a flow passage, through which a fluid flow containing particles can pass, and an exterior surface portion to receive light passed by the focusing optical system. The surface portion of the flow cell, which operatively receives light passed by the focusing optical system, is not orthogonal to the optical axis of the system.

Another aspect of the present invention is directed to a particle analyzing apparatus for discriminating particulate element(s) in a fluid flow for purposes of analysis, classification, sorting, and presentation. The apparatus includes an illumination source to emit an illumination beam, a flow cell, a sample supply, a focusing optical system, and a light sensor. The flow cell has a flow passage extending through the flow cell, a rear surface portion that receives an illumination beam emitted by the illumination source, and a forward surface portion that passes light formed from an illumination beam received by the rear surface portion. The sample supply functions to introduce a fluid to the flow passage of the flow cell. The focusing optical system, positioned between the illumination source and the flow cell and having an aperture, forms and positions a beam waist of an emitted illumination beam relative to the flow passage. The first light sensor operates to receive light passed by the flow cell. The illumination beam source emits an illumination beam having an intensity profile characterized by a central, principal intensity peak that originates and terminates at substantially null intensity values. With respect to a synchronized relationship of elements of the system, the flow cell is further arranged relative to the illumination source so that the principal intensity peak is substantially centered with respect to the flow path, and such illumination beam intercepts internal boundaries of the flow cell, which define the flow path, proximate to the null intensity values.

An object of the present invention is to provide an optical system having a synchronized illumination beam and flow cell.

Another object of the present invention is to provide an optical system having a flow cell oriented to control back reflection when subjected to an illumination beam.

Another object of the present invention is to provide a particle analyzing apparatus, to discriminate particles in a fluid flow for analysis, classification, sorting, and presentation, having a flow cell-light sensor relationship to enable a gathering of a specific range of light scatter passed by the flow cell, such specific range of light scatter directly corresponding to at least one type of particle capable of being identified.

Another object of the present invention is address the objects of this invention, whether individually or in combination, and maintain an appropriate overall apparatus size.

Other objects and advantages of the present invention will be apparent to those of ordinary skill in the art having reference to the following specification together with the drawings.

BRIEF DESCRIPTION OF THE DRAWINGS

Referring now to the drawings in which like reference numerals and letters indicate corresponding elements throughout the several views, if applicable.

DETAILED DESCRIPTION OF THE PREFERRED EMBODIMENTS

Various embodiments, including preferred embodiments, are described in detail below with reference to the drawings.

Figures 2A, 2D, 2E:
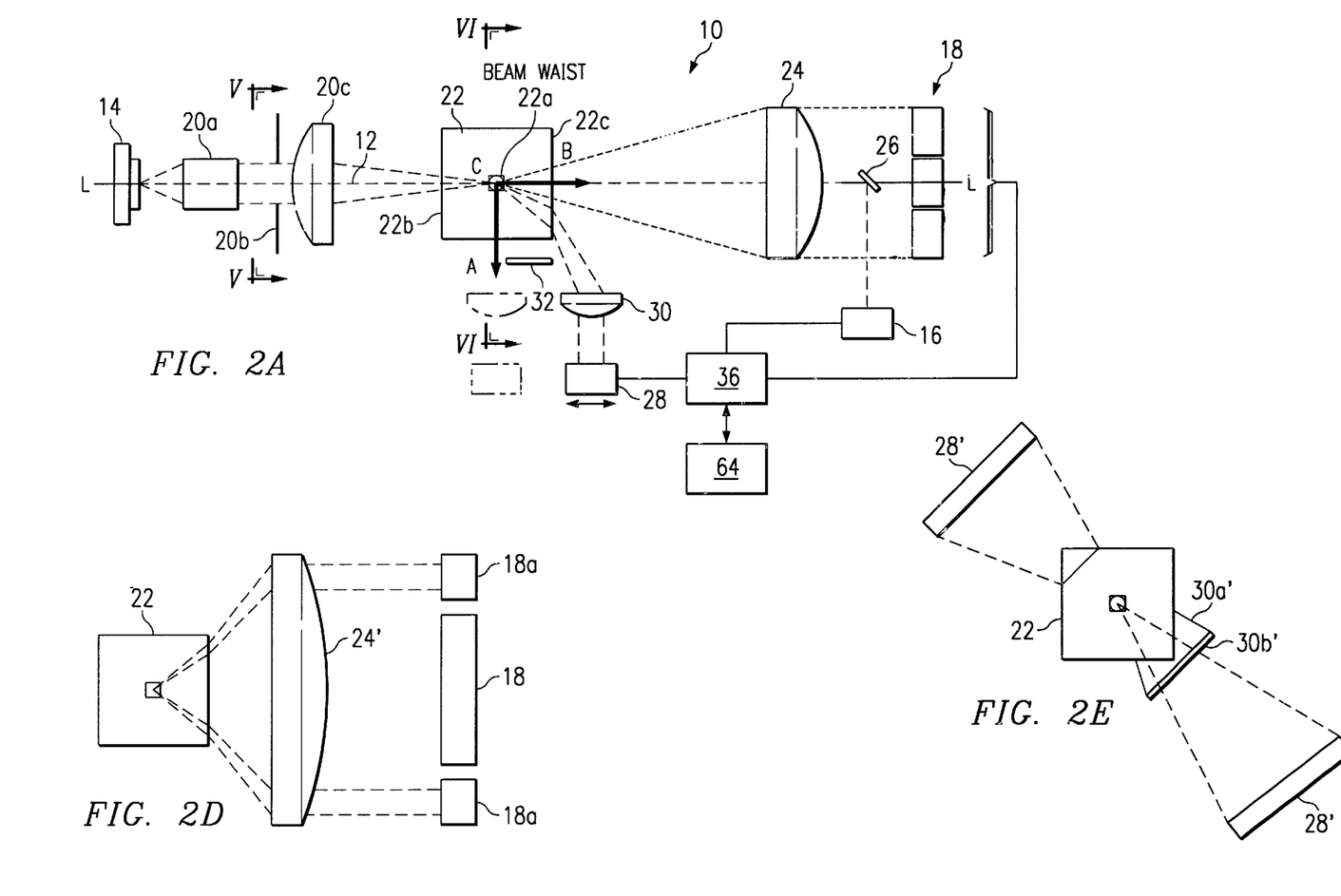
FIG. 2A is a schematic view of a particle discrimination apparatus in accordance with the present invention.
FIGS. 2C, 2D, and 2E illustrate alternative configurations for a flow cell and light scatter sensor of FIG. 2A.

FIG. 2A illustrates a particulate element (or particle) discrimination apparatus 10 in accordance with the present invention. The apparatus 10 is effectively defined along a path 12 (or axis-L) that extends between a laser source 14 and a plurality of light scatter sensors 16 and 18.

The laser source 14 can be any one of a plurality of conventional lasers suitable for this application, for example, a low power helium-neon laser. In a preferred embodiment, the laser source 14 is a solid-state laser diode.

A laser beam emitted from the laser source 14 passes through a focusing optical system 20, e.g., a collimating lens 20a, an aperture structure 20b, and a focusing lens 20c, before reaching a flow cell 22. This laser path is in reference to the illustrated axis-A and axis-B as well as an axis-C', which is substantially normal to the page illustrating FIG. 2A, that corresponds to a fluidic center of the flow cell 22.

Figure 3:
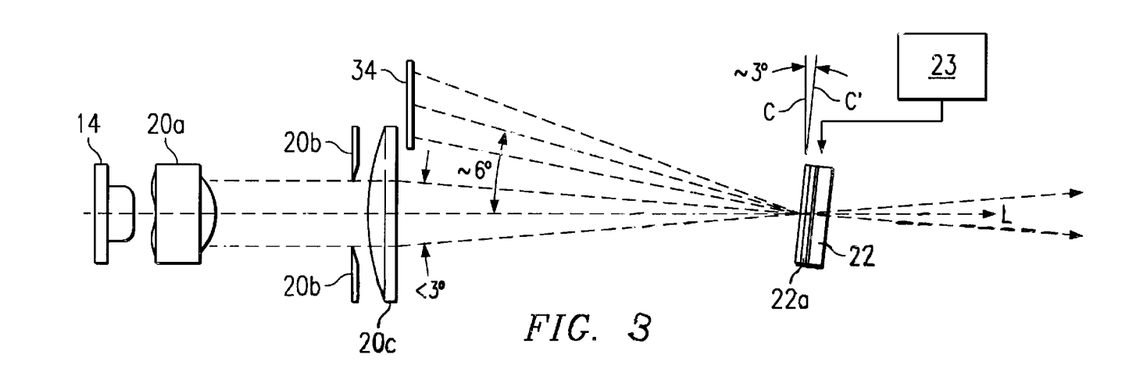
FIG. 3 illustrates a variation of the particle discrimination apparatus of FIG. 2A.

As illustrated, the flow cell 22 includes a flow path 22a, in accordance with axis-C', in which flows a hydrodynamically focused fluid filament that contains particulate elements to be discriminated. The flow path 22a is in fluid communication with a fluid source 23, which typically holds a diluted sample for delivery to the flow cell 22 (FIG. 3). The flow cell 22 is formed of an optically transparent material, for example, quartz in the form of strain-free fused silica, or the like. Although the flow cell 22 could take a partially arcuate form, a preferred form of the flow cell 22 is one of the readily available flow cytometry flow cuvettes having parallel sides. In particular, the flow cell 22 has a square shape with a complementary square-shaped flow path 22a. However, the perimeter shape of the flow path 22a is not optically dictated by the exterior shape of the flow cell 22. Accordingly, irrespective of the exterior shape of the flow cell 22, the flow path 22a of the flow cell 22 can assume a rectangular or other shape conducive to maintaining a position of a particulate element carrying fluid filament, which flows therethrough, relative to an illumination beam as well as at least those walls of the flow path 22a that are parallel to axis-B of FIG. 2A.

Returning to the arrangement of the apparatus 10 of FIG. 2A, a second optical system 24, e.g., a collection lens, is provided optically downstream from the flow cell 22. The optical system 24 collects and passes a prescribed portion of light scatter generated from a laser beam, emitted from the laser source 14, striking a particle passing through the flow path 22a.

From each particulate element struck by an incident laser beam emitted from the laser source 14, light is scattered in all spherical directions over $4\pi$ steradians. Therefore, such scattered light encircles the particle carrying fluid filament equatorially. In every application of particle flow analysis, it is necessary, allowing for the actual walls of the flow cell 22, to identify and capture that light scatter which provides pertinent information regarding the nature of the scatter-producing particulate element(s). The optical system 24 is used to gather that pertinent portion of the requisite light scatter and pass it to one or more of a plurality of light sensors, for example, sensors 16, 18, and 28. Consequently, in the equatorial circle about the particle carrying fluid filament, the combination of light sensors 16, 18, and 28 (discussed below) can receive light from 0° ("axial light loss," "extinction," or "beam monitor") to almost 180° ("backward scatter"), wherein such angular values are in reference to an emitted laser beam. In a preferred pure scatter embodiment, the combination of light sensors 16 and 18 can collectively receive any light scatter passed by the optically-downstream face of flow cell 22 of FIG. 2A.

Although the multi-angle laser light scatter (MALLS) sensors 16, 18 can be combined in a single sensor array (not shown), it is equally possible to separate the light sensors 16 and 18. The need to separate the light sensors could be due to physical space limitations, for example, imposed by a production-type device. In the event separated light sensors 16 and 18 cannot conveniently capture certain specific MALLS light, it is necessary to direct that certain specific light scatter to a specifically positioned light sensor. An example of this structure is illustrated in FIG. 2A.

Specifically, a mirror 26 is illustrated that is capable of intercepting and passing at least axial light scatter to the light sensor 16. In a preferred embodiment, the mirror 26 intercepts and passes axial light fluctuation (0°) to the light sensor 16. Although the illustration concerns axial light fluctuations, the mirror 26 could be positioned elsewhere relative to the output of the optical system 24 to reflect another specific range of light scatter to a receiving light sensor. Further yet, the structure of element 26 could alternatively be a receiving face of an optical fiber, which would function to capture a specific range of light scatter and direct it to a corresponding light sensor.

In FIG. 2A, an illustrated light sensor 28 is positioned relative to the flow cell 22 to receive a particular range of light scatter output from the flow cell 22. It is intended that this particular range of MALLS light scatter provide information not otherwise cost-effectively discernable from the approximately 360 degree MALLS light scatter sensors 16 and 18.

When using the apparatus 10 as a hematology analyzer, for example, this particular range can specifically relate to abundant sub-micron granules in particular subpopulations of biological cells (e.g., eosinophillic granulocytes) to be discriminated. Accordingly, while the particular range of light depends on the characteristics of the particle, in a preferred embodiment, the light sensor 28 receives a range of light scatter from 25°–50° (such angle being with respect to an axis of the flow cell 22). In a more preferred embodiment, the light sensor 28 receives a range of light scatter from 30°–45°. In a most preferred embodiment, the light sensor 28 receives a range of light scatter from 35°–43°. The illustrated position of the light sensor 28 is characterized by its light receiving surface being substantially parallel to a surface of the flow cell 22, such surface being effectively perpendicular to the axis-A.

In regard to application of the common mode rejection ratio technique, as discussed in the background section of this disclosure, the light sensor 28 can appreciably provide at least first and second robust and light scatter. The basis of the implicit common mode compensation in a two-angle design is that, if appreciable systematic background scattering error still occurs for the first sensor 18 (for example, at 13°) and the sensor 28 (for example, at 37°), then a reasonably-constant-function background error will be introduced into both of the outputs of sensors 18 and 28 and these errors should leave any cell cluster position contrasts in related, generated biplot scattergrams reasonably unaffected. Thus, real differences between, for example, the sub-micron granules of such granulocytes as neutrophils, eosinophils, and basophils, should be far more apparent than if only a single scatter measurement is resorted to at any one of the MALLS locations between 13° and 90°0.

At each edge of the flow cell 22, it is possible to specify two very exact angular locations. For example, at the 45° corner of a square flow cell (e.g., FIG. 2A), the 37° location (below the 45° position) and the 53° location (above the 45° position) Consequently, the disclosed positional relationship between sensor 28 and the flow cell 22 enables exact and reproducible positioning to collect that light scatter which enables application of the common mode rejection ratio technique.

While the light sensor 28 can be fixed in position, FIG. 2A illustrates that the light sensor 28 and the optical lens 30 system can also be movable from an illustrated position (i.e., a first position) to a position substantially centered with axis-A of the flow cell 22 (i.e., a second position). In such a second position, the light sensor 28 can receive "orthogonal" light scatter passed from the flow cell 22—a popular and traditional range for detection in walled-conduit flow cytometry after it was discovered in the 1970's that background laser scatter from flow cell edges raised the limit of MALLS particulate detection from light scatter to above one micron. Of note, the ray stop 32 is illustrated for the movable sensor 28 variation of the present invention and not for the use of sensor 28 to intercept orthogonal light scatter.

In a preferred embodiment using the movable sensor 28, the ray stop 32 would preferably also be movable so as to function in a manner complementary to the movement of the light sensor 28. Specifically, when the light sensor 28 is in the first position, the ray stop 32 would be in place to extinguish unwanted light scatter, and when the light sensor 28 is in the second position, the ray stop 32 would be withdrawn from its illustrated position to avoid interfering with the receipt of orthogonal light scatter.

As illustrated, however, the ray stop 32 is positioned so as to purposely extinguish a range of light scatter that might otherwise interfere with the sensing of a particular range of light scatter output from the flow cell 22 and receivable by the light sensor 28. The ray stop 32 can be a largely opaque, independent member positioned relative to the flow cell 22 or adhered to the flow cell 22, a film (not shown) applied to the flow cell 22, or an applied pigmentation (not shown).

While the above description is directed to a new structural arrangement between the light sensor 28 and the flow cell 22 that facilitates cost-effective and reliable positioning and consistent reception of a subset of MALLS, there are other alternative arrangements for intercepting desired MALLS. However, in view of the spherically symmetric behavior of ray paths from an optic centroid, the arrangement of components 28,30, and 32 of FIG. 2A can readily be transposed, together with mirror imaging at each corner, to any of the four corners of the flow cell shown in FIG. 2A. One such example of a transposition is shown in FIG. 2C.

FIG. 2D illustrates a structural arrangement adapted to collect a particular sub-range of light scatter with an additional forward light sensor array 18a. For such arrangement, it is necessary to position a collection lens 24' very near to an exiting face of the flow cell 22. Irrespective of the position of the collection lens 24' relative to the flow cell 22, such collection lens 24' must have a dimension greater than the collection lens 24 of FIG. 1A. Consequently, increasing the size of the collection lens 24 can undesirably increase both costs and a physical size of the apparatus 10.

FIG. 2E illustrates a structural arrangement adapted to collect the desired sub-range of light scatter with one or more light sensors 28' arranged with respect to the corners of the flow cell 22. Prior to the light sensors 28', a structure is provided that includes a material 30a', having a refractive index substantially equal to that of the flow cell material, and a glass cover 30b'. While such structure is suited for collecting the prescribed light scatter, the structural relationship between the flow cell 22 and the sensor 28' is more complex than utilization of the corner relationship of sensor 28 in FIG. 2A (or FIG. 2C), thus requiring greater accuracy in placement and more elaborate constructions in manufacturing to minimize angular detection differences between instruments.

As mentioned above, the laser source 14 is preferably a solid-state laser diode. Using a laser diode enables the optical path between the laser source 14 and the flow cell 22 to be significantly shortened in comparison to the minimum focal distance needed for other sufficient laser sources, e.g., a helium-neon laser. Thus, the overall size of the apparatus 10 can be made smaller.

In order to obtain the most accurate light scatter results, it is important to obtain a maximum signal-to-noise ratio, in the broad, conventional sense. In a more specific, narrower technical sense, this corresponds to minimizing detection of limiting background light and maximizing a signal-to-noise ratio. "Signal" is defined as a "net signal," i.e., a gross mean signal minus mean background signal, and metrologic "noise" is defined narrowly as the root mean square fluctuation of the gross signal about the mean gross signal.

The signal, in accordance with the above definitions, can be severely compromised by light reflected from any surface of the flow cell 22, or even from certain particle streams, back into the laser cavity of the laser source 14. In some cases, only a small amount of reflected light can cause noise modulation within the laser cavity and effect a signal-to-noise ratio, in accordance with the above definition, below 1%. Of course, even the potential for such an event is not acceptable.

In general regard to the optical elements of the apparatus 10, it is common practice to minimize unwanted reflections from an optical surface by applying an anti-reflection coating to the respective optical surface. While such coatings are preferably applied to each of the optical systems of the present invention, application of an anti-reflection coating to the optically upstream surface 22b and optically downstream surface 22c of the flow cell 22 is not easily achieved. Due to its small dimensions (e.g., 4 mm), it is notably difficult to apply optical coatings uniformly to the outer surfaces of the flow cell 22. Coating attempts are therefore costly, and may not perform to desired specifications.

Consequently, reference is made to FIG. 3, which illustrates a particularized embodiment of the present invention. In a preferred embodiment, a direction of fluid flow through the flow path 22a is axially aligned with axis-C', which is angularly displaced approximately 3° from axis-C, where axis-C is orthogonal to both axis-A and axis-B (FIG. 2A). Notwithstanding this preferred inclination, axis-C' can be angularly displaced from axis-C to any angular value between approximately 2.5° and approximately 15°.

As an alternative, the direction of fluid flow of the flow path 22a is again axially aligned with axis-C'; however, axis-C' is maintained strictly vertical (for optimal gravitational fluid flow control or bubble control) and the sensor 28 and axis-C, which remain substantially parallel, are tilted by a prescribed amount (not shown), for example, approximately 3°, relative to axis-C'. As yet another alternative, the direction of fluid flow of the flow path 22a is axially aligned with axis-C, positioned which is strictly orthogonal to both axis-A and axis-B (FIG. 2A). However, axis-A and/or axis-B of flow cell 22 could be rotated by approximately 3.0° about axis-C. While not illustrated, that would result in: a rotation from colinearity with axis-L and/or a rotation from the horizontal orthogonal with respect to axis-L. As will be discussed in greater detail below, such slight rotation is not incompatible with avoiding flow cell edge illumination and thus avoiding its associated light scatter.

While the flow cell 22 can receive an anti-reflective coating, to avoid the uncertainty and expense of such coatings, the flow cell 22 is preferably uncoated. To this end, an uncoated, polished face of the flow cell 22, which does not include the edges of such face, reflects approximately 4% of an approximately orthogonally received light at each glass-air interface.

Additional light can be reflected from the internal flow cell surfaces and even from the hydrodynamically focused particulate filament if there are certain differences between sample and sheath streams. If even a small portion of this reflected light were to return to the laser source 14, it would substantially increase the likelihood of light fluctuations and beam noise.

Because of the angular displacement of the flow cell 22 of FIG. 3, back light reflection is not received by the laser source 14. In accord with the illustrated example, the 3° tilt of the flow cell 22 causes the centerline of the reflected beams to be approximately 6° from the axis-L at any single reflection surface. Since the extent of the beam in the vertical direction is less than 3°, the closest (i.e., the illustrated lowest) ray from the reflected beam will be greater than 3° away from the highest ray of the illuminating beam. As shown, a beam dump 34 is preferably provided to extinguish any back reflections by the flow cell 22.

Critical to obtaining repeatable discrimination results from the detected light scatter, it is very important that the illumination of each particle be both constant and consistent. To achieve this, each particle must pass through the illumination beam (i.e., laser beam) as close to the mean path as possible, and the light intensity must be as near uniform as possible in the area of the mean path.

As emphasized in FIGS. 1A–1D, maintaining a course for each particle along a constant narrow flow path 22a is accomplished by hydrodynamically focusing the sample using a surrounding particle-free sheath fluid. The method of U.S. Pat. No. 3,871,770 was an improvement over long-known earlier methods. These earlier methods suffice to provide excellent hydrodynamic flow stability in a walled conduit of the preferred embodiment, especially if both sample and sheath are driven by positive displacement pressure as by separate syringes. Use of such known methods for the present invention maintains the course of each particle through the sensing region, or "sensing cylinder," of the flow cell 22 within a centralized flow filament that can be made arbitrarily narrow in diameter. For a preferred embodiment, a 250 $\mu$m×250 $\mu$m flow path 22a receives a fluid filament of approximately 25 $\mu$m in diameter for the application of white cell synfocal multi-angle laser light scatter (SMALLS) interrogation.

Operationally, unless there are monitored bubble or inflow malfunctions, a fluid filament does not commonly wander by more than its diameter from its central mean position within the flow path 22a. Notwithstanding, any significant flow degradation is readily reduced via well-known principles, for example, an increase in the coefficient of variation of available mono-sized monitoring latex particles.

As outlined in FIGS. 1A–1B, using sophisticated methods of particle alignment addresses only one issue. For sub-micron MALLS, it is even more important to control the placement and background quality and noise quality of laser illumination. In the context of at least the present invention, one aspect of laser noise is addressed by that arrangement illustrated in FIG. 3. Further, to minimize other historically debilitating laser noise and to lower the enormous background noise associated with traditional laser application using walled conduits such as that common to the present invention, the preferred laser source 14 and focusing optical system 20 are arranged to center a focal point of a precisely dimensioned illuminating beam, i.e., a beam waist (FIG. 2B), with respect to the flow path 22a of the flow cell 22.

Figure 2B:
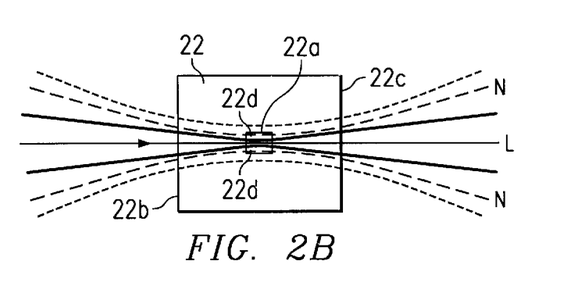
FIG. 2B shows a localized view of the flow cell of the particle discrimination apparatus of FIG. 2A.
Figure 2C:
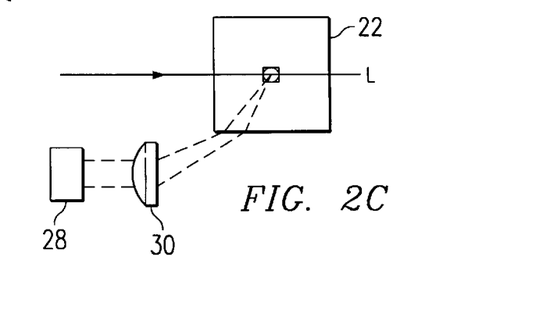

The primary and secondary optical aberrations are well controlled in the optical elements that comprise the focusing optical system 20 to form an illumination beam having an intensity profile that is "diffraction limited." In such instance, the laser beam will have a beam waist as illustrated in FIG. 2B. Additionally, the intensity profile of the illumination beam at the beam waist is substantially in accordance with equations for optical diffraction. This intensity profile can also be deduced from mapping a cross-section of the illumination beam at the beam waist.

Figure 6:
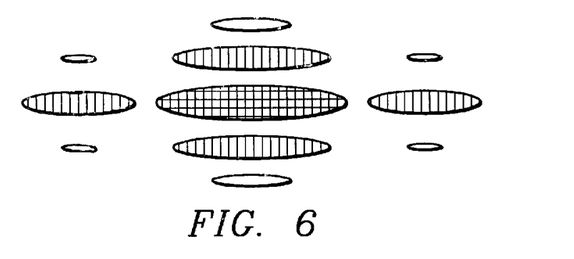
FIG. 6 illustrates a cross-section of an illumination beam emitted from a laser source of a particle discrimination apparatus of FIG. 2A, such illumination beam having an intensity profile in accordance with FIG. 4.

FIG. 6 shows such an experimentally determinable light density profile section, the section being taken in a plane A–C of FIG. 2A, without showing the related structure of the flow cell 22. Each of the visible intensity spots shown here is like a Gaussian peak rising from the page, with the illustrated hatching of each spot suggesting the relative density of the peak symbolized by that spot. Thus, the doubly-hatched central peak characterizes the most intense illumination while the peripheral peaks are much less intense.

Figure 4:
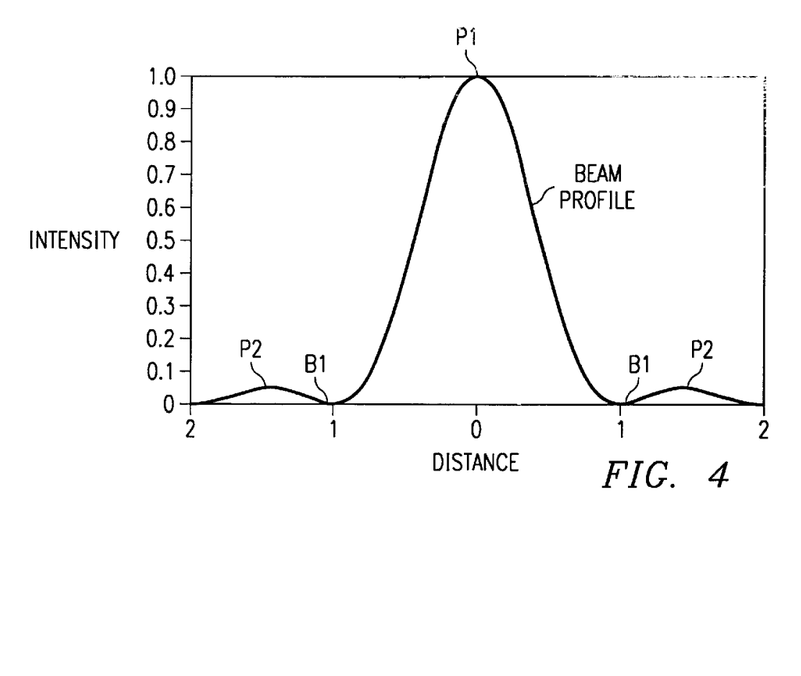
FIG. 4 shows one embodiment of an illumination beam intensity plot for a laser beam emitted from a laser source of the particle discrimination apparatus of FIG. 2A.
Figure 5:
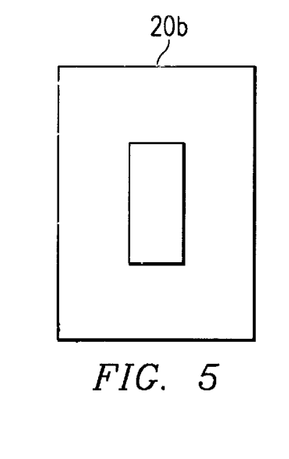
FIG. 5 illustrates an aperture of the particle discrimination apparatus of FIG. 2A, such view being taken along line V—V.

FIG. 4 shows this light intensity relationship in another way. FIG. 4 can be conceived as a section through the three central intensity peaks of FIG. 6. Specifically, ignoring the materials and refractions at the flow cell 22 itself, the intensity profile of the illumination beam in accordance with the present invention can be written as:

$$I = \{\sin(\pi \cdot W \cdot x / \lambda \cdot f) / (\pi \cdot W \cdot x / \lambda \cdot f)\}^2 \qquad \text{Equ. (1)}$$

where, x represents the distance value corresponding to an optical spot size formed by an illumination beam emitted from the illumination source, $\lambda$ represents a wavelength of such illumination beam, f represents the focal length of the focusing subsystem, and W is a width dimension of the aperture of the aperture structure 20b (FIG. 5). A plot of this intensity profile is shown in FIG. 4. In reference to this figure, the ordinate conveys an intensity value in relation to a relative cross-section dimension of an optical spot.

In appreciation of Equ. (1), the dimensions of a beam profile are accurately and reliably determined by two optical parameters of the system: a focal ratio (or F-number) and a wavelength of the illumination beam. The F-number is a ratio of the focal length of the focusing optical system 20 to the width dimension of the aperture of the aperture structure 20b.

In reference to the aperture structure 20b of FIG. 5, it is preferred that its aperture be of a rectangular form. While other aperture shapes (e.g., circular, elliptical, square, etc.) are permissible and would enable proper functionality of the present invention, a rectangular shape conventionally allows independent control of the F-number parameters in both horizontal and vertical directions.

As an example of one possible configuration of the present invention, the longitudinal dimension of a rectangular aperture, as illustrated in FIG. 5, is approximately 0.635 mm, which results in a corresponding focal ratio of approximately 157:1 and a spot size of approximately 100 $\mu$m. In general accordance with the plot of FIG. 4, the intensity at 125 $\mu$m from the center of the beam center is only about 3.2% of the maximum intensity of the illumination beam.

Again referring to FIG. 4, an illumination beam profile is characterized by a principal, central intensity peak (P1) that originates and terminates at two nulls (or bottoms) (B1). In each axis of the aperture of FIG. 5, two significantly lesser intensity peaks (P2) are symmetrically positioned along the outer peripheries of the illumination beam and their exact position can be designated by computation. In accordance with the computed plot of FIG. 4, FIG. 6 depicts a simplified, computed cross-section, having vertical and horizontal components, of the illumination beam at the beam waist.

As stated above, it is desirous for a particle subject to illumination to pass near the central intensity peak of the illumination beam. In order for a particle to pass through the illumination beam where the intensity of the illumination beam is at least 95%, however, the particle must pass within approximately 12% of the optical spot size of the center of an illumination beam. To improve the chances of such particle-illumination beam relationship for any given particle, it is conventional practice for designers of such optical systems to select parameters that would result in the formation of a very large optical spot size. For example, the illuminating laser beam and laser beam waist could be symbolized by any of the three bands in FIG. 2B or even by a very narrow beam lying entirely within the axis-L of FIG. 2B. Such narrow beams are known in systems such as those of Eisert et al (U.S. Pat. No. 4,110,043) or Wyatt et al (U.S. Pat. No. 4,616,927)

However, as indicated in the context of FIG. 1D, formation of a large optical spot size (as symbolized by the outside band in FIG. 2B) has been more typical in applications such as flow cytometry; and that has adversely affected the pure scattering signal-to-noise ratio of such systems. In regard to the potential signal component of the ratio, a large optical spot size (i.e., beam waist) has a reduced central beam intensity, which results in a diminished light scatter signal. Thus, for any given laser source, the signal-to-noise and signal to background ratio would be adversely affected by use of a large optical spot size.

Further, concerning a background light component, when an optical spot size is greater than the dimensions of the flow path 22a, strong light scatter is produced from an interaction between the illumination beam and the edges/internal corners of the flow path 22a (FIG. 2B). Unfortunately, meaningless background light scatter produced from such interaction is significantly more intense than light scatter produced from an interaction between the illumination beam and a sub-micron particle passing through the flow path 22a. As intense background light scatter reduces the ability of a system to discern valuable information from the net signal MALLS light scatter, some devices have employed elaborate screening and rejection methods against tolerated signal degrading walled-conduit light scatter (see U.S. Pat. Nos. 4,577,964 and 5,125,737). Although the approach in U.S. Pat. No. 4,577,964 did permit sensitive optic counting of human platelets and U.S. Pat. No. 5,125,737 patent does provide certain light scatter information for large human leukocytes at a selected light scatter locus via a walled conduit scatter sensor of the type of FIG. 1D, neither approach, which tolerates very high non-specific background scatter, can be a basis for general MALLS interrogation of sub-micron particles, as these particles are below the optic scatter detection threshold of these scattering systems examples.

In accordance with the present invention, the above background scatter problems of the conventional art are avoided. In particular, the focal ratio of the lens 20c positions a center of the principal intensity peak (P1) of the illumination beam profile at a point approximately in a center of the flow path 22a with respect to the width dimension between the internal side walls of the flow cell. Moreover, the nulls (B1) are arranged to proximally coincide with the internal boundaries/corners 22d of the flow path 22a, thus the intense walled-conduit background light scatter of FIG. 1D is minimized. Of note, such positioning can be achieved even if the approximately straight walls of the flow path 22a are not totally parallel to the axis B of FIG. 2A. To better illustrate the "synfocal" principle of this synchronized focusing aspect of the present invention, reference is made to FIG. 7.

Figure 7:
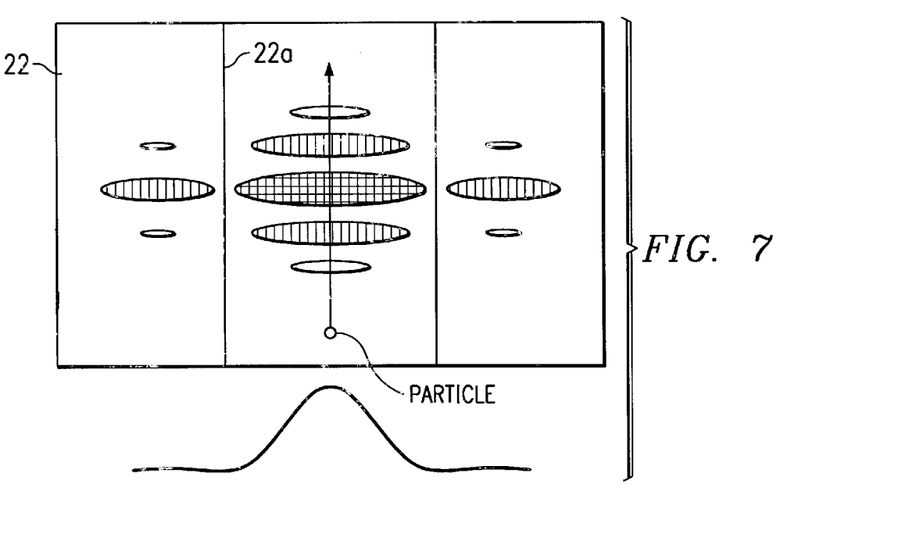
FIG. 7 illustrates a cross-section of the flow cell of the particle discrimination apparatus of FIG. 2A with illumination beam cross-section, as taken along line VI—VI.

Here particles flow in a hydrodynamically focused, centralized fluid filament through the flow cell 22 from bottom to top. The illumination beam, being normal to the page on which the illustration is made, is shown in cross-section. This beam intercepts the flow cell 22 and illuminates particles as they flow centrally through the flow cell 22.

The energy profile of FIG. 4 is shown below the flow cell 22 section to exhibit the synchronization of the laser beam null intensities B1 with the scattering walls and edges 22d of the flow cell 22. This nadir or bottom B1 of the energy profile is also illustrated in FIG. 2B as path N.

Signals produced by the various directionally selected light sensors 16, 18, 18a, 28, and 28' are supplied to an analyzing device 36, which functions to convert such supplied signals to information regarding the nature of particles detected by the above-described optical system. As the present invention is principally drawn to the above-described optical system, the analyzing device 36 is not critical to the present invention. To this end, any analyzing-type device that is responsive to signals produced, whether electrical, scatter, polarization, fluorescence, infrared, radio waves, or the like, is appropriate.

In the context of hematology analyzers, the particles to be discriminated can be populations or subpopulations of supra-micron biological cells ranging, in order of native size, from monocytes through neutrophils, basophils, eosinophils, lymphocytes and erythrocytes down to thrombocytes as described in part in U.S. Pat. Nos. 5,017,497, 5,138,181, or U.S. Pat. 5,378,633. Additionally, in the context of hematology analyzers, the particles to be discriminated can also be ensembles of sub-micron cell organelles and substructures probably ranging, in native size down to around 400 nm as described in many U.S. patents to Philip Wyatt in the 1970's and 1980's in the context of various highly specialized, expensive wall-avoiding flow analysis systems.

Moreover, in principle the present invention can be used to detect the reticulum of reticulocytes, the resting or contracted microtubular whoop of thrombocytes, certain sub-structure morphologies of stem cells and most of those sub-micron structures that have been detected or characterized successfully by scatter with the diverse research systems which have avoided adverse wall illumination background scatter. Moreover, in the context of such hematology analyzers, discrimination of particles can be performed by the above-described optics alone, or in combination with other conventional particle discrimination tools, for example, Coulter apertures and/or Coulter DC and/or RF signal processing.

Figure 8:
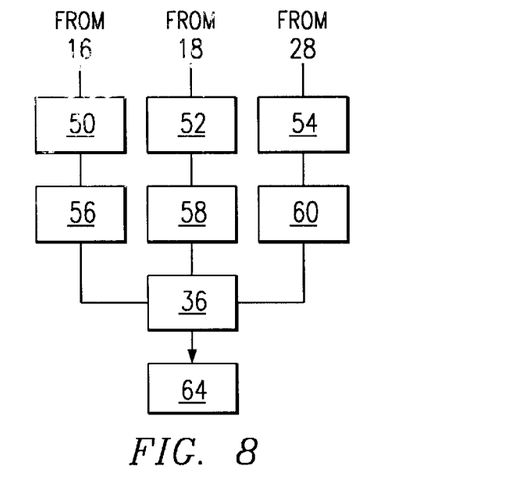
FIG. 8 is a schematic view of one embodiment of an analyzing device for discriminating particles, based on light scatter, for sorting and presentation.

FIG. 8 illustrates one possible example of an analyzing device 36 for a hematology analyzer. Each of the respective outputs, for example, from the sensors 16, 18, and 28 are supplied to amplification circuit(s) 50, 52, and 54 that respectively can include amplifiers, filters, pulse shapers, and the like. Processed signals are supplied to signal peak detectors 56, 58, and 60 before passing to analyzer 62. For this example, the analyzer 62 includes a series of analog comparators (not shown) that compare the input signals from the peak detectors 56, 58, and 60 to predetermined values that are individually representative of specific subpopulation members of biological cells. Output from the comparators can be counted, for preparation of histograms or matrices, or combined in at least two-member groupings, for purposes of preparing scattergrams. Output from the analyzer 62 is supplied to a display device 64 (e.g., printer, CRT, etc.).

Of note, many types of known additional particle interrogation mechanisms (and applications, such as cell sorting) were discussed in the background portion of this disclosure. Though incorporated by reference, those not benefiting directly from our invention(s) to reduce MALLS background scatter and laser noise are not displayed in the figures of our teachings. However, the different aspects of the present invention individually and jointly enable cost-effective SMALLS analysis in many settings and for many different applications and may be equally applied to such.

While the invention has been described herein relative to a number of particularized embodiments, it is understood that modifications of, and alternatives to, these embodiments, such modifications and alternatives realizing the advantages and benefits of this invention, will be apparent to those of ordinary skill in the art having reference to this specification and its drawings. It is contemplated that such modifications and alternatives are within the scope of this invention as subsequently claimed herein, and it is intended that the scope of this invention claimed herein be limited only by the broadest interpretation of the appended claims to which the inventors are legally entitled.

What is claimed is:

1. A particle analyzing apparatus for discriminating particulate element(s) in a fluid flow for purposes of analysis, classification, sorting, and presentation, the apparatus having an illumination source for emitting an illumination beam, the apparatus comprising:

a flow cell having a flow passage through which a fluid flow containing particles can pass, a first exterior face perpendicular to a first axis of the flow cell, and a second exterior face perpendicular to a second axis of the flow cell, wherein the first axis is substantially co-axial with an illumination beam emitted from the illumination source, the flow passage is positioned between the illumination source and the first exterior face, and the first exterior face and the second exterior face are orthogonal; and a light sensor to receive light from the illumination source via the flow cell, the light sensor being oriented substantially parallel to the second exterior face of the flow cell and displaced a sufficient distance from the second axis in a direction in parallel with the first axis to enable receipt of a prescribed range of light passed by the first exterior face.

2. An apparatus in accordance with claim 1, further comprising light extinguishing means that is adapted to intercept and extinguish at least a portion of any light passed by the second exterior face.

3. An apparatus in accordance with claim 1, further comprising a focusing optical system, positioned between the illumination source and the flow cell, to position a beam waist of an emitted illumination beam within the flow passage.

4. An apparatus in accordance with claim 1, wherein the illumination source is a solid-state laser diode.

5. An apparatus in accordance with claim 1, wherein the illumination source emits an illumination beam having an intensity profile characterized by a substantially central, maximum intensity peak.

6. An apparatus in accordance with claim 5, wherein the flow cell is arranged relative to the illumination source so that a maximum intensity peak of an emitted illumination beam is substantially centered with respect to the flow passage, and such illumination beam intercepts internal edges of the flow cell that define the flow path at points that generate a minimal light scatter.

7. An apparatus in accordance with claim 6, wherein the internal edges intercept the illumination beam at or about intensity nulls of the illumination beam.

8. An apparatus in accordance with claim 1, wherein the flow cell is not orthogonal to an illumination beam emitted by the illumination source.

9. An apparatus in accordance with claim 1, wherein the flow cell is displaced by an angle relative to a direction orthogonal to an illumination beam emitted by the illumination source, and the angle is between 2.5°–10°.

10. An apparatus in accordance with claim 9, further comprising a focusing optical system, positioned between the illumination source and the flow cell, to position a beam waist of an emitted illumination beam within the flow passage.

11. An apparatus in accordance with claim 1, further including at least one additional light sensor, positioned substantially orthogonal to an axis of an illumination beam emitted by the illumination source, to receive light from the illumination source via the flow cell.

12. An apparatus in accordance with claim 1, wherein the light sensor is movable and is adapted to move between a first position and a second position, the second position being substantially centered with the second axis.

13. A particle analyzing apparatus for discriminating particulate element(s) in a fluid flow for purposes of analysis, classification, sorting, and presentation, the apparatus comprising:

an illumination source to emit an illumination beam;

a flow cell having a flow passage extending through the flow cell, a rear surface portion that receives an illumination beam emitted by the illumination source, and a forward surface portion that passes light formed from an illumination beam received by the rear surface portion;

a sample supply to introduce a fluid to the flow passage of the flow cell; and a light sensor to receive at least light passed from the flow cell in response to an interaction with an illumination beam emitted by the illumination source and a fluid supplied to the flow passage of the flow cell, wherein the flow cell has a first axis, which is substantially co-axial with an axis of an illumination beam emitted from the illumination source, and a second axis, which is orthogonal to the first axis, and wherein a light receiving surface of the light sensor is substantially parallel to the axis of an illumination beam emitted from the illumination source, and the light sensor is displaced a prescribed distance from the second axis to enable receipt of a prescribed range of light passed by the forward surface portion.

14. An apparatus in accordance with claim 13, further comprising light extinguishing means that is adapted to intercept and to substantially prevent passage of at least a portion of light passed by the flow cell toward the first light sensor.

15. An apparatus in accordance with claim 13, further comprising a focusing optical system, positioned between the illumination source and the flow cell, to form and to position a beam waist of an emitted illumination beam within the flow passage.

16. An apparatus in accordance with claim 13, wherein the illumination source is a solid-state laser diode.

17. An apparatus in accordance with claim 13, wherein the flow cell is arranged relative to the illumination source so that a maximum intensity peak of an illumination beam emitted by the illumination source is substantially centered with respect to the flow passage, and such illumination beam intercepts internal edges of the flow cell, which define the flow path, at points that yield a minimum light scatter.

18. An apparatus in accordance with claim 17, wherein the internal edges intercept the illumination beam at or about intensity nulls of the illumination beam.

19. An apparatus in accordance with claim 13, wherein the flow cell is not orthogonal to an illumination beam emitted by the illumination source.

20. An apparatus in accordance with claim 19, further comprising a focusing optical system, positioned between the illumination source and the flow cell, to form and to position a beam waist of an emitted illumination beam within the flow passage.

21. An apparatus in accordance with claim 13, wherein the flow cell is displaced by an angle relative to a direction orthogonal to an illumination beam emitted by the illumination source, and the angle is between 2.5°–10°.

22. An apparatus in accordance with claim 13, further including a second light sensor, positioned substantially orthogonal to an axis of an illumination beam emitted by the illumination source, to receive light from the illumination source via the flow cell.

23. An apparatus in accordance with claim 13, wherein the light sensor is movable to and from the prescribed distance from the second axis, and a second position, the second position being substantially centered with the second axis.

24. A particle analyzing apparatus for discriminating particulate element(s) in a fluid flow for purposes of analysis, classification, sorting, and presentation, the apparatus having an illumination source for emitting an illumination beam along an optical axis of the apparatus, the apparatus comprising:

a flow cell having a flow passage through which a fluid flow containing particles can pass, a first exterior face perpendicular to a first axis of the flow cell, and a second exterior face parallel to the first exterior face, wherein the flow passage is positioned between the illumination source and the first exterior face; and a light sensor, oriented substantially parallel to the second exterior face of the flow cell and displaced a sufficient distance from the optical axis to enable receipt of a prescribed range of light passed by the first exterior face of the flow cell, wherein the first axis is substantially co-axial with the optical axis.

25. A method for optically differentiating at least one type of particulate element carried by a fluid filament, the method comprising the steps of:

providing a laser source and a flow cell, the flow cell having a flow passage through which a fluid flow containing particles can pass, a first exterior face perpendicular to a first axis of the flow cell, and a second exterior face that is orthogonal to the first exterior face, wherein the flow passage is positioned between the illumination source and the first exterior face; and providing a first light sensor, oriented substantially parallel to the second exterior face of the flow cell and displaced a sufficient distance from a centralized, normal axis of the second exterior face in a direction parallel to the first axis to enable receipt of a first prescribed range of light passed by the first exterior face;

providing a second light sensor to receive a second prescribed range of light passed by the flow cell;

emitting a laser beam from a laser source along an optical path and through the flow cell during passage of a fluid filament through the flow passage;

sensing at least a portion of light scatter, using the first light sensor, produced by an interaction between a particulate element, carried by the fluid filament, and the laser beam; and compare data representative of light scatter sensed by the first light sensor and data representative of light scatter sensed by the second light sensor and, based on such comparison, identify common data representative of light scatter formed independent of the interaction between the particulate element and the laser beam.

26. A particle analyzing apparatus for discriminating particulate element(s) in a fluid flow for purposes of analysis, classification, sorting, and presentation, the apparatus having an illumination source for emitting an illumination beam, the apparatus comprising:

a flow cell having a flow passage through which a fluid flow containing particles can pass, a first exterior face perpendicular to a first axis of the flow cell, and a second exterior face perpendicular to a second axis of the flow cell, wherein the first axis is substantially co-axial with an illumination beam emitted from the illumination source, and the first exterior face and the second exterior face are orthogonal; and a light sensor to receive light from the illumination source via the flow cell, the light sensor being oriented substantially parallel to the first exterior face of the flow cell and displaced a sufficient distance from the first axis in a direction in parallel with the second axis to enable receipt of a prescribed range of light passed by the second exterior face.

27. An apparatus in accordance with claim 26, further comprising a focusing optical system, positioned between the illumination source and the flow cell, to position a beam waist of an emitted illumination beam within the flow passage.

28. An apparatus in accordance with claim 26, wherein the illumination source is a solid-state laser diode.

29. An apparatus in accordance with claim 26, wherein the illumination source emits an illumination beam having an intensity profile characterized by a substantially central, maximum intensity peak.

30. An apparatus in accordance with claim 29, wherein the flow cell is arranged relative to the illumination source so that a maximum intensity peak of an emitted illumination beam is substantially centered with respect to the flow passage, and such illumination beam intercepts internal edges of the flow cell that define the flow path at points that generate a minimal light scatter.

31. An apparatus in accordance with claim 30, wherein the internal edges intercept the illumination beam at or about intensity nulls of the illumination beam.

32. An apparatus in accordance with claim 26 wherein the flow cell is not orthogonal to an illumination beam emitted by the illumination source.

33. An apparatus in accordance with claim 26, wherein the flow cell is displaced by an angle relative to a direction orthogonal to an illumination beam emitted by the illumination source, and the angle is between 2.5°–10°.

34. An apparatus in accordance with claim 33, further comprising a focusing optical system, positioned between the illumination source and the flow cell, to position a beam waist of an emitted illumination beam within the flow passage.

35. An apparatus in accordance with claim 26, further including at least one additional light sensor, positioned substantially orthogonal to an axis of an illumination beam emitted by the illumination source, to receive light from the illumination source via the flow cell.

36. An apparatus in accordance with claim 26, wherein the light sensor is movable and is adapted to move between a first position and a second position, the second position being substantially centered with the second axis.

* * * * *